United States Patent [19]

Catsimpoolas

[11] 4,375,401
[45] Mar. 1, 1983

[54] ELECTROPHORESIS SYSTEM

[76] Inventor: Nicholas Catsimpoolas, 65 Montvale Rd., Newton Center, Mass. 02159

[21] Appl. No.: 265,425

[22] Filed: May 20, 1981

[51] Int. Cl.$^3$ .................... B01D 13/02; G01N 27/28
[52] U.S. Cl. ................................ 204/301; 204/299 R
[58] Field of Search ........................... 204/301, 299 R

[56] References Cited

U.S. PATENT DOCUMENTS

| | | | |
|---|---|---|---|
| 3,867,271 | 2/1975 | Hoefer | 204/299 R |
| 4,048,049 | 9/1977 | Hoefer | 204/299 R |
| 4,061,561 | 12/1977 | Grunbaum | 204/299 R |
| 4,124,470 | 11/1978 | Dahms | 204/180 G |
| 4,130,471 | 12/1978 | Grubaum | 204/180 G |
| 4,199,428 | 4/1980 | Hayashi et al. | 204/299 R |

*Primary Examiner*—Howard S. Williams

[57] ABSTRACT

An improved electrophoresis system for simple, rapid and reproducible separations of biological materials such as proteins, nucleic acids, cells, bacteria, cell organelles, etc. is described. The system consists of several subsystems including a first dimensional system having a multi-column rotatable carousel with automatic density gradient maker and sample deposition, a unique fraction collector cassette which can serve as a sample applicator for the second dimension electrophoresis and a slab-gel second-dimensional electrophoresis system. The total system operation is integrated by microprocessor control. Flexibility in the system design and operation allows for running in an analytical or preparative mode at the discretion of the system operator.

18 Claims, 16 Drawing Figures

1ST. DIMENSION ELECTROPHORESIS (AUTOMATIC)
BLOCK DIAGRAM

1ST. DIMENSION ELECTROPHORESIS (AUTOMATIC) BLOCK DIAGRAM

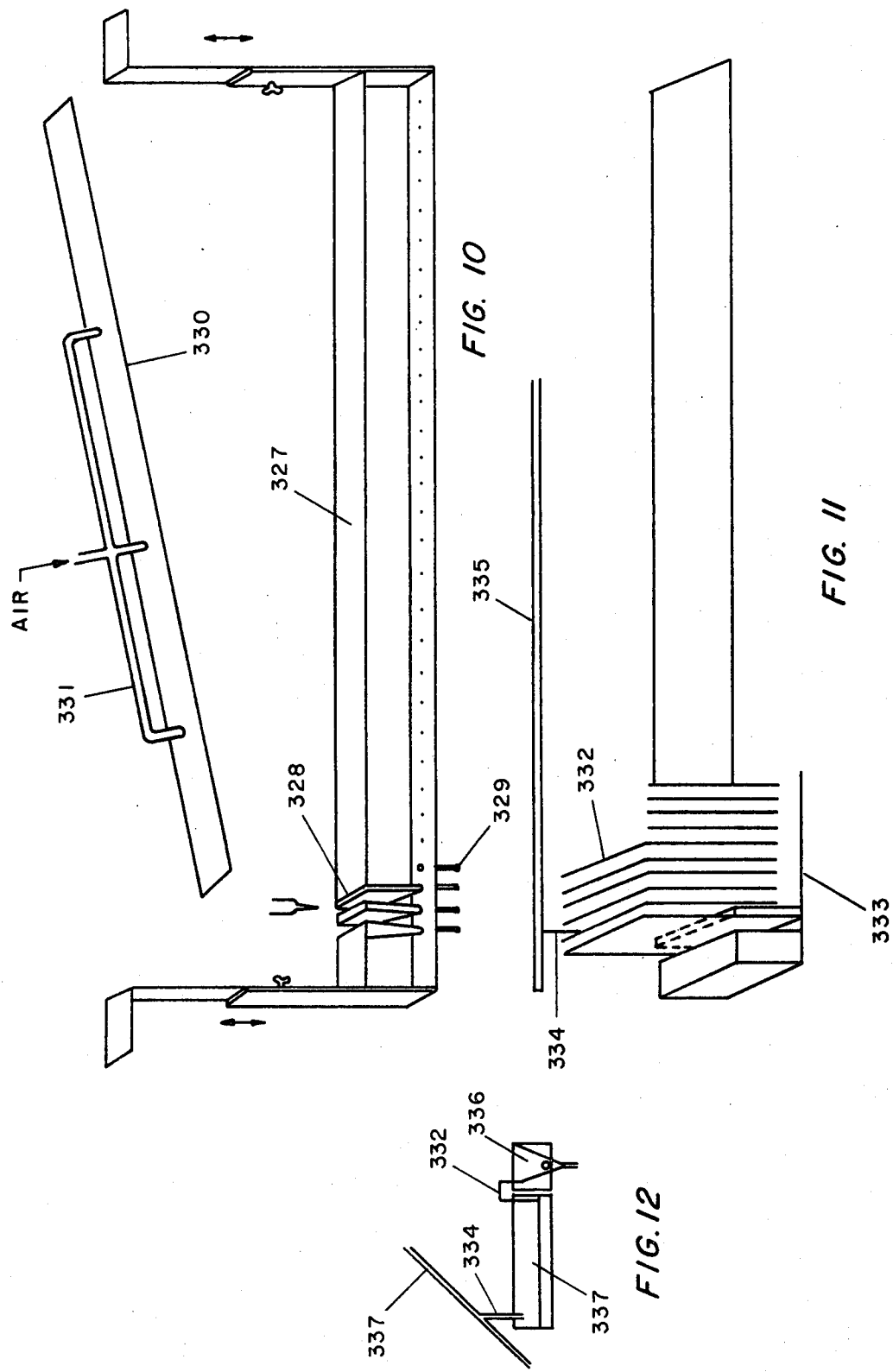

ELECTROPHORESIS SYSTEM

BACKGROUND OF THE INVENTION

In U.S. Pat. No. 4,124,470 there is described an automatic apparatus for zone or density gradient electrophoresis. The apparatus utilizes a turntable onto which are loaded empty electrophoresis tubes which are filled in serial fashion with sample and electrophoresis medium utilizing an automatic diluter. Each of the tubes has conductive means at both ends and when voltage is supplied an electrophoretic pattern is produced in the tubes. The turntable transports the tubes from the loading station to a scanning station while the electrophoresis separation is proceeding. The electrophoretic patterns are scanned by means of an optical probe which is dipped into the electrophoresis tube without disturbing the bands. Other types of protein (isoenzymes) are measured after dispensing of a selective reagent.

A tube gel electrophoresis device is described in U.S. Pat. No. 4,048,049 which comprises a number of concentrically mounted gel tubes. The tubes extend between an upper buffer chamber and a lower buffer chamber. The lower buffer chamber is operatively connected to a cooling core so as to provide heat transfer during the electrophoresis. An advantage ascribed to this apparatus is that it may be assembled or disassembled without draining the buffer and coolant. Morever the individual tubes may be removed from the assembly during operation without similar draining of the buffer and cooling chambers. A variety of gel tube sizes can be accommodated by using interchangeable upper buffer chambers. The tubes do not rotate during operation but remain fixed in their relative positions. A similar multiple tube gel electrophoresis apparatus for handling a number of samples simultaneously is disclosed in U.S. Pat. No. 3,867,271.

In U.S. Pat. No. Re. 27,552 an apparatus for density gradient electrophoresis is described. An important feature of this apparatus is the use of electrodes immersed in electrolytes disposed near the top and the bottom of the vertical gradient tube. Semi-permeable membranes are utilized to permit ionic current flow from the electrolyte solutions to the fluid columns contained within the vertical tube while isolating such solutions from the columns.

U.S. Pat. No. 4,199,428 provides a sample feeder which can be used for sequentially delivering multiple samples to a sample applicator of an electrophoresis system.

An automatic multiple-sample applicator for a two-dimensional gel electrophoresis system is described in U.S. Pat. No. 4,061,561. The multiple-sample applicator coacts with a tank cover allowing an operator either to depress a single button thus causing multiple samples to be simultaneously deposited on the gel or to depress one or more sample applicators separately by means of a separate button for each applicator. The sample applicator picks up multiple specimens from corresponding wells in the sample holder using capillary action to fill when contact is made by the applicator with the fluid surface. The electrophoretic gel is held in a tray and the samples are transferred to the gel through the applicator tips. These tips can cut into the gel and thus they eliminate the need for prepared slot formation on the gel.

U.S. Pat. No. 4,130,471 provides a microelectrophoretic apparatus and process which employs a multi-sample applicator capable of applying 10 samples consecutively or simultaneously and is adapted to be used with the apparatus of U.S. Pat. No. 4,061,561 discussed above for two dimensional gel electrophoresis.

Alternative systems used in the art to provide continuous electrophoretic separations in an automated mode utilized moving belts or film covered with the electrophoretic medium and sample disposed on one surface and passing the belt or film through the electrophoretic chamber. Representative systems of this type of arrangement are found in U.S. Pat. No. 3,133,009 (coated tape); U.S. Pat. No. 3,896,021 (cellulose acetate coated tape); U.S. Pat. No. 4,059,501 (coated moving belt) and U.S. Pat. No. 4,198,284 (pair of endless belts carrying sample on film).

BRIEF SUMMARY OF THE INVENTION

The objective of the electrophoretic system of the present invention is to provide a convenient, rapid and reproducible means for performing high-resolution, preparative or analytical electrophoresis in an automated manner and with second dimension capability. The total system consists of a number of sub-systems or sub-units combined into an automated microprocessor controlled system. The objective of ease of operation is accomplished by:

(1) providing automatic media preparation for the first dimensional electrophoresis;
(2) utilizing multiple, automatic sample application for both dimensions;
(3) automatically controlling parameters of operation such as cooling, fluid flow, movement of fractions, cleaning, and sterilization solutions, etc.

The objective of speed is met by use of a multiple column system which processes up to twelve samples per complete revolution. In addition automatic media preparation (1st dimension) and the availability of pre-prepared media as articles of commerce greatly reduces the time for the overall operation.

The object of reproducibility is accomplished by employing fully automated conditions and sequence controls of electrophoresis and the standardized format and grid locator used for precise identification and quantitation.

The first dimensional system utilizes isoelectric focusing or electrophoresis, or isotachophoresis using density gradients in glass columns. These columns are supported in circular configuration within a rotating concentric turntable or carousel. Means are provided to allow needed fluid flow of buffers and cooling solution throughout the rotational cycle during which electrophoresis of the sample takes place. Distinct stations are provided at selected points in the carousel to effectuate one of the following functions:

Deposition of gradient density solution in column
Deposition of sample/deposition of buffers
Electrophoresis
Gradient/fraction evacuation and monitoring
Washing, rinsing and drying columns.

In a preferred embodiment the assemblies and components of the first dimensional system include the following:

1. Gradient density maker;
2. Sample applicator;
3. Buffer applicator;
4. Carousel assembly and motor;
5. Cooling assembly;
6. Cleaning apparatus assembly;

7. Power supply assembly;
8. Evacuation monitor assemblies;
9. Fraction collector assembly;
10. Recorder assembly;
11. Microprocessor control assembly.

The fraction collector assembly is of a novel design and construction which allows up to about 50 discrete fractions to be retained in a single holder. The holder comprises up to 50 individual sample chambers which are each in fluid flow connection with a corresponding individual capillary sample applicator. When an air tight cover is inserted over the holder and pressure applied, the individual fraction samples are applied directly to a second dimension electrophoresis gel in preselected and uniformly distributed positions. In cases where the fractions provided to the fraction collector are monitored by UV or pH, and thus the various volumes in the individual sample chambers are non uniform, a novel multi-element siphoning system is provided to equalize the volumes so as to allow uniform sample quantities to be used in the second dimension electrophoresis.

The fraction collector holder is designed and constructed so as to be attachable to the tank which holds the electrophoretic gel slabs or the slabs themselves for the purpose of properly distributing the fractions to the gel in their appropriate places. Preferably the tank will accommodate the same number of slabs as the number of gradient columns in the carousel of the first dimensional system. Thus all fractions which are collected from a run on the first dimensional system can be transferred in a single operation and run simultaneously in the second dimensional system. Up to six hundred separate fraction samples can be run in this manner during one cycle of the total system. The fraction collector holder is removed after sample application and prior to initiation of the second dimension electrophoresis.

Basic elements which comprise the second dimensional system include the following:
tank
electrophoresis media
sample applicator
cooling system
visualization process
power supply
controls.

Additional objects and features of the invention will appear from the following description in which the preferred embodiment has been set forth in detail in conjunction with the accompanying drawings.

BRIEF DESCRIPTION OF THE DRAWINGS

FIG. 10 is a front view of the fraction collector sample holder with pressure manifold cover.

FIG. 11 is a front view of the sample volume equalizer with vacuum manifold.

FIG. 12 is a side view of the sample volume equalizer.

DESCRIPTION OF THE PREFERRED EMBODIMENT

The preferred embodiment of the present invention is more readily understood by reference to the aforesaid Drawings.

Figure 1:
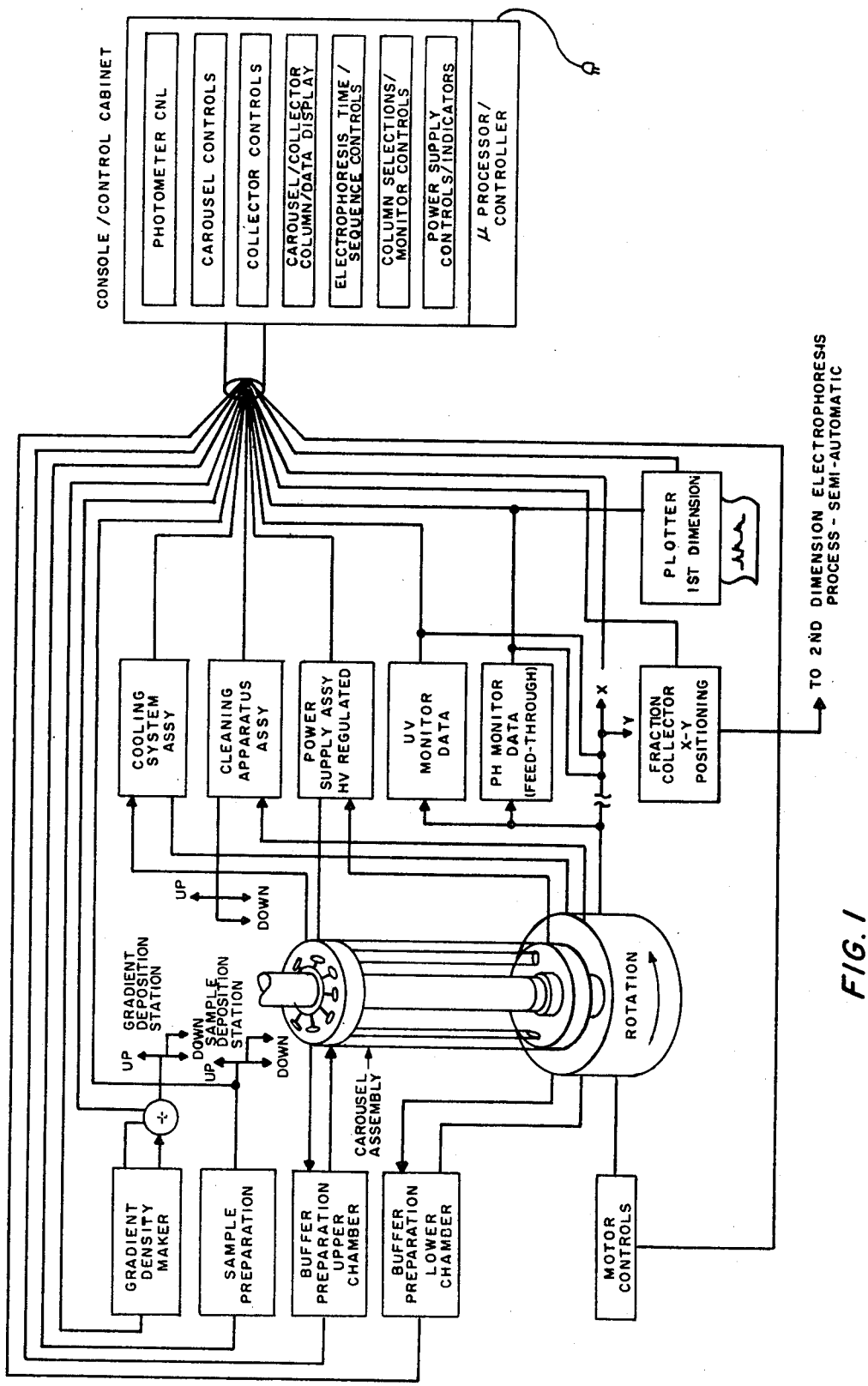
FIG. 1 is a schematic block diagram representation of the first dimensional system showing control interactions between the main subcomponents.

In FIG. 1 there is shown a block diagram depicting the main assembly components of the first dimension electrophoresis system and the control elements providing manual or automatic operation. The microprocessor will provide a complete sequence of events needed to complete the first dimension electrophoresis processes. The microprocessor monitors and controls all functions to be performed and designates the time sequence for each event. In addition to sequence controls monitored by the aforesaid microprocessor, the system is provided with manual controls which can override the microprocessor with respect to certain steps in the process. Such manual controls include:
Photometer control
Carousel controls including controls for manually advancing the carousel to a specific, desired location, a home control which relocates the carousel to provide column #1 to station #1, which is the gradient density solution disposition station, and control for forward and reverse direction of the carousel Collector controls for manual X-Y positioning of the fraction collector Carousel/Collector Column/Data Display Electrophoresis Time/Sequence Controls for individual setting of the time for electrophoresis Column Selection/Monitor Controls Power Supply Controls to control voltage level at electrodes.

Additional controls not shown but which can be employed, if desired, include controls for cleaning the carousel, reservoirs, and monitoring/collecting tubing and controls for controlling flow of the cooling system.

As seen in FIG. 1 rotation of the carousel assembly is carried out by activation of the motor control by signals provided either by the microprocessor under automatic control or from the manual carousel controls discussed above. A stepping motor is utilized in the preferred embodiment to effect the rotation from station to station. When a twelve column carousel is used then an equivalent number of stations are provided and the stepping motor provides a 30° rotation per step.

The initial station in the first dimension electrophoresis system is the gradient disposition station. When an empty, cleaned electrophoresis inner column on the carousel is positioned at this station and the gradient making cycle is initiated under microprocessor control the gradient deposition station applicator is put in the activated or down position to provide a fluid flow conduit between the gradient density maker, and the carousel inner column at station #1. The gradient density maker mixes solutions such as sucrose of Ficoll of selected densities (i.e. 5% to 40%) to generate a solution that has a density which varies linearly between the aforesaid limits at a predetermined rate. The solution is then deposited in the inner column of the carousel assembly. During the gradient density application, the carousel assembly is stationary until the gradient is completely deposited and the applicator is lifted up to its stand-by position. Particular details about the construction and operation of the gradient deposition station are provided later in the specification.

The second station in the carousel rotation cycle is the sample desposition station. In a preferred embodiment the sample is withdrawn from a conventional individual sample holder cuvette within a sample collector by using a device employing X-Y positioning. The sample is then deposited in the inner tubes in the carousel after the particular column was filled with the gradient density and shifted to the next station for sample application. As was the case with the gradient density applicator, the application of the sample is again done by means of an up/down control that positions the applicator nozzle into the inner tube, just above the previously deposited gradient solution.

To avoid mixing of samples between applications, the sample applicator should be cleaned completely before the next sample application to avoid contamination and mixing. Further details of the construction and operation of the sample applicator station are provided below.

Activation of the stepping motor and rotation of the carousel to the next station which provides a flow of buffer solution to the upper chambers and lower chambers of the carousel. The buffer solutions are stored in two reservoirs, one for each of the aforesaid group of chambers. In the carousel, the buffer solution provides ionic contact between the electrode assemblies at each of the columns and the semipermeable membranes which provide isolation between the sample containing gradient solution and the buffer. Both lower and upper buffer chambers in each column have separate inlet/outlet ports that allow filling and emptying the buffers as well as recirculating the buffer solutions during the electrophoresis process.

The electrophoresis is initiated when the carousel is rotated to the next (fourth) station. A high voltage potential is applied across the electrodes under control of the power supply control. This potential is maintained during the entire electrophoresis procedure even during column rotation from station four to station ten.

When the subject column is rotated to station eleven the electrophoresis has terminated and under control of the collector controls the contents of the electrophoresis tube is evacuated through the lower collector and fractions taken by the fraction collector assembly. Fraction cut-off can be pre-set on a volume basis, i.e., fractions are taken after a predetermined number of milliliters are evacuated or alternatively the electrophoresis medium can be monitored by one or more desired parameters such as ultraviolet absorption or pH and fraction cuts made when these parameters change by predetermined amount. The fraction collection assembly is capable of obtaining up to 50 discrete fractions from each individual column. Thus during one complete carousel cycle a total of 600 fractions can be collected.

The fraction collector assembly utilizes X-Y positioning and up/down sequence controls to provide deposition of fractions to a designated fraction collector cuvette, most preferably in a uniquely designed cuvette contained in a multiple sample holder adapted to be attached to the slab gels used for the second dimensional electrophoretic separation.

Rotation of the carousel to the next station places the subject column within operating relationship to the cleaning apparatus assembly. The cleaning apparatus is used to provide cleaning solution and water to flush out and clean the inner tube in the carousel assembly after the fractions have been evacuated. The cleaning solution is preferably applied into the tube by means of a nozzle-sprayer combination that is lowered into the inner tube at the cleaning station. The cleaning solution exits from the lower part of the inner tube through the sample lines connecting the chambers to the fraction collector into a waste disposal tank.

Preferably hot air is also used at the end of the cleaning process. The cleaning process and the timing are all gated with the process sequence controls.

At this point the emptied and cleaned column is rotated back to station one in readiness to start the entire electrophoresis process over again. Alternatively, the entire carousel can be disengaged and replaced after sterilization should infectious materials, such as virus or bacteria, be in the sample media.

It should be noted the cooling system serves to provide cooling liquid to the space between the inner and outer tubes in the column assembly of the carousel. The cooling liquid, e.g. water at about 4° C., is circulated, preferably countercurrently, such as by entering through the lower port connector, then through the outer column and out through the upper port. Cooling liquid circulates through the outer column during the entire rotational cycle of the carousel assembly.

As indicated above, the specific construction and operation of the various assemblies and components of the first dimensional system are described in greater detail below.

Figure 2:
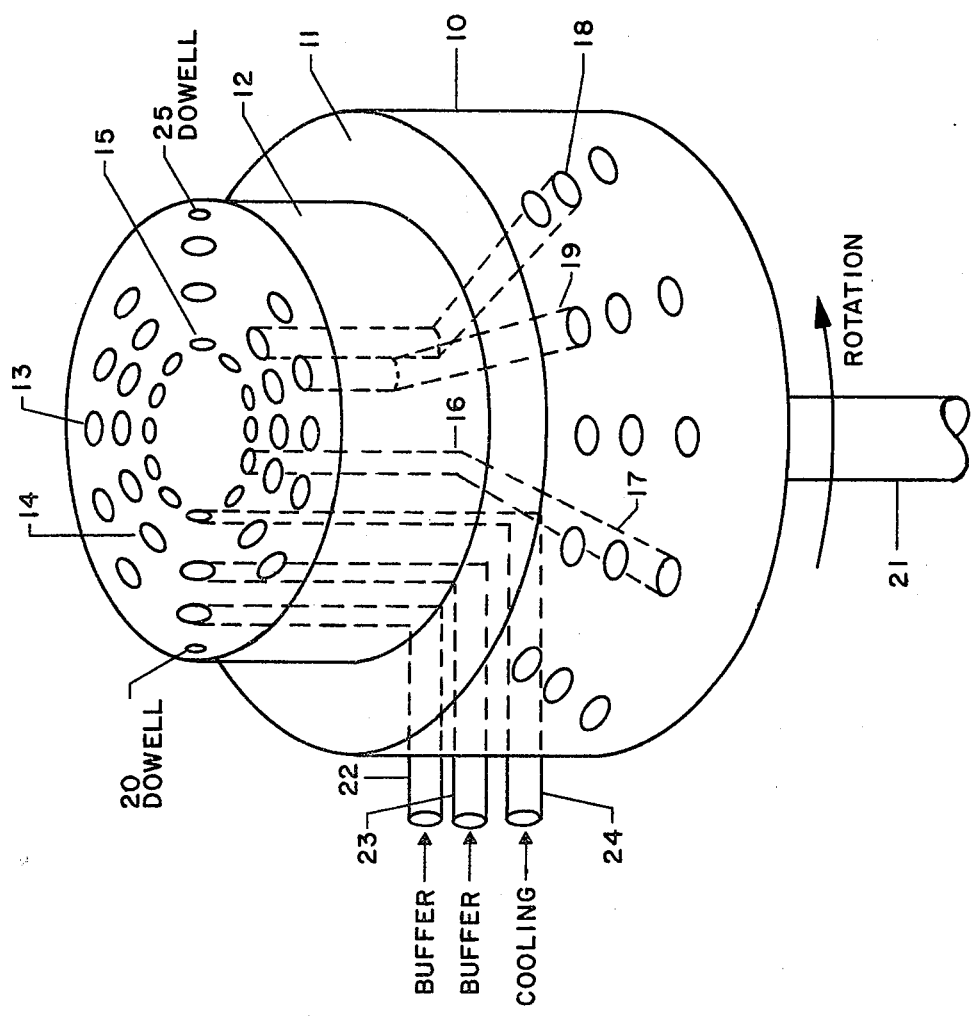
FIG. 2 is an isometric view of the upper collector assembly of the first dimensional system carousel which provides continuity of flow during operational rotation.

Turning now to FIG. 2, an isometric view of the upper collector assembly of the first dimensional electrophoresis carousel is presented. This assembly provides the means for continuous fluid flow connection between the external fluid lines and the electrophoresis and cooling tubes during rotation via a stationary outlet port (not shown) which is slidably attached to the top of the upper collector. The upper collector is formed from a major cylindrical section 10 and a cylindrical section of smaller circumference 12 which is affixed onto the major section. A shelf 11 is thus formed on the top surface of section 10.

Twelve channels formed in each of three concentric ring conformations are provided in cylindrical section. The inner channel ring containing representative channel 15 is adapted to provide cooling fluid derived from an external reservoir through a stationary upper port assembly (to be described later) through the channel and then through a perpendicularly oriented channel 17 in cylindrical section 10 via bend 16. Similarly the middle channel ring containing representative channel 14 provides a buffer inlet into the upper electrode chamber via perpendicular channel 18. Finally, the outer channel ring containing representative channel 13 provides a fluid outlet for the buffer flow from the upper electrode chamber via perpendicular channel 19. Fluid flow conduits such as representative conduits 22 (linking the outer channel ring), 23 (linking the middle channel ring) and 24 (linking the inner channel ring) emanate spoke like from the upper collector assembly and provide fluid flow connection with the top inlets of the twelve electrophoresis tubes which circumferentially surround the upper collector assembly.

At other positions around the circle corresponding to different stations in the electrophoresis cycle the buffer inlet and outlet functions are replaced by fluid flow associated with fraction evacuation, column cleaning and drying. Complementary functions are provided in the lower collector assembly at the other end of the carousel assembly.

The upper collector assembly rotates with the carousel as it is mounted on the central shaft 21 which is linked to the stepping motor. Dowells 20 and 25 are provided to allow convenient mounting of the two cylindrical sections.

Figure 3:
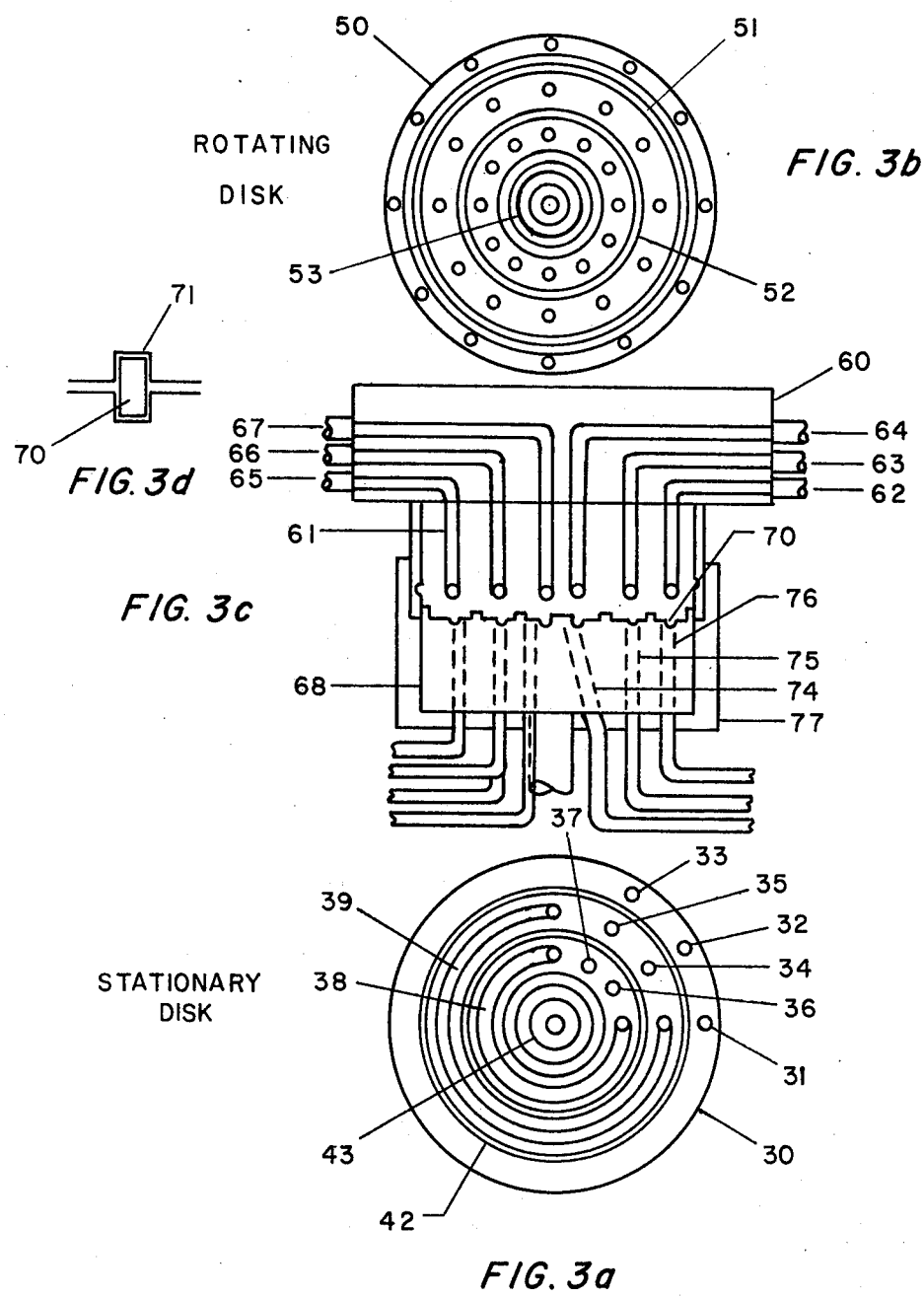
FIG. 3a is a view of the engaging surface of a stationary disk or surface which engages the rotating portion of the carousel and by means of positioned groove and hole openings serves to control fluid flow during rotation.
FIG. 3b is a view of the engaging surface of a rotating disk or surface which engages the stationary disk or surface and contains a series of concentric holes which provide fluid flow connections for the various functions associated with the electrophoresis processes.
FIG. 3c is a cross-sectional view of the lower collector assembly showing the fluid inlets and outlets for the carousel and the assembled stationary and rotating disks.
FIG. 3d is a cross-sectional detail view of the stationary and rotating disks showing the Teflon ring washer used to provide isolation between adjacent rings of holes in each disk.

FIG. 3 provides several views of the components which make up the lower collector assembly and the stationary and rotating disks or surfaces which provide fluid flow control during rotation of the carousel through its cycle. Thus in FIG. 3a a view of the engaging surface of a stationary disk component is shown. This can be in the form of an independent element or can be constructed on the engaging surface of the lower port.

In FIG. 3a the stationary disk 30 is seen to be divided into a series of 4 rings of concentric holes or grooves surrounded by inert washers serving to preserve the separate fluid flow integrity of each ring. The other ring of holes such as representative holes 31, 32 and 33 provide individual connections from each column and thus represent stations where the contents of the individual electrophoresis columns are evacuated. Thus, hole 31 can be used to remove the sample containing gradient column while holes 32 and 33 can be used to pass through the wash solution and drying materials.

The next two rings represent the buffer out and buffer in rings respectively. Thus, open groove 37 will allow buffer to flow out continuously through rotation of the carousel through stations during which the electrophoresis is taking place. Similarly, open groove 38 allows buffer to flow up into the lower electrode compartment. Grooves 37 and 38 have the identical radial arc in their respective rings as they will each be open to fluid flow during the exact same positions of the rotational cycle. The innermost groove 43 allows coolant flow to pass throughout passage to all stations in the cycle.

Holes 34 and 35 in the second ring and holes 36 and 37 in the third ring are used to provide buffer cleaning to the electrode chamber at the cleaning station. Each of the rings are maintained in fluid tight relationship to each other by use of washer rings interposed between the operating rings, e.g. washer rings 41, 42 and 43. These washers can be made of any suitable inert plastic material such as Teflon.

FIG. 3b shows a view of the engaging surface of a rotating disk or surface. This disk 50 has four concentric rings of holes. Each of the rows contains twelve holes which are arranged and constructed to be in operative flow relation with the electrophoresis cycle stations and have the same orientations as the grooves and holes in the stationary ring with which they are intended to engage. Grooves 51, 52 and 53 provide a means to engage the washers.

Similarly, disk 50 can be in the form of an independent element or can be constructed on the engaging surface of the smaller cylindrical section of the lower collector.

In FIG. 3c, a cross-sectional view of the lower collector assembly is shown. Analogous to the upper collector previously discussed in FIG. 2, the lower collector comprises a major cylindrical section 60 and an affixed cylindrical section of smaller circumference 61. The fluid conduits 62, 63, 64, 65, 66 and 67 are representative of the connectors which run from the bottom inlets of the individual electrophoresis tubes and again run spoke like to the central lower collector. These channels again made a 90° bend and pass through the cylindrical section 61. Lower outlet port 68 is firmly affixed to cylindrical section 61 by means of screw cap 77. The outlet port 68 remains stationary while the lower collector assembly comprising sections 60 and 61 rotates with the entire carousel assembly of which they are an integral part.

The interface 69 between the lower collector and the outlet port is comprised of the disks shown in FIGS. 3a and 3b. The stationary disk of FIG. 3a is situated contiguous with the inner face of the outlet port 68, while the rotating disk of FIG. 3b is mounted on the inner face of cylindrical section 61 of the lower collector. The two disks or the entire assembly are made of a material such as stainless steel or precision cast plastic which allows them to be slidably engaged with each other. As the rotating disk moves circularly with the rotation of the carousel the concentric rings of holes make or break fluid flow connections between the channels of the lower port 68 and the corresponding channels in cylindrical section 61 depending on whether the holes or grooves are engaged in the stationary disk.

As shown in FIG. 3d a washer ring 70 preferably Teflon is inserted in a groove on the faces of stationary disk 71 and rotating disk 72 so as to provide complete isolation between the various rings and thus eliminate mixing of fluids or fluid loss during operation.

Figure 4:
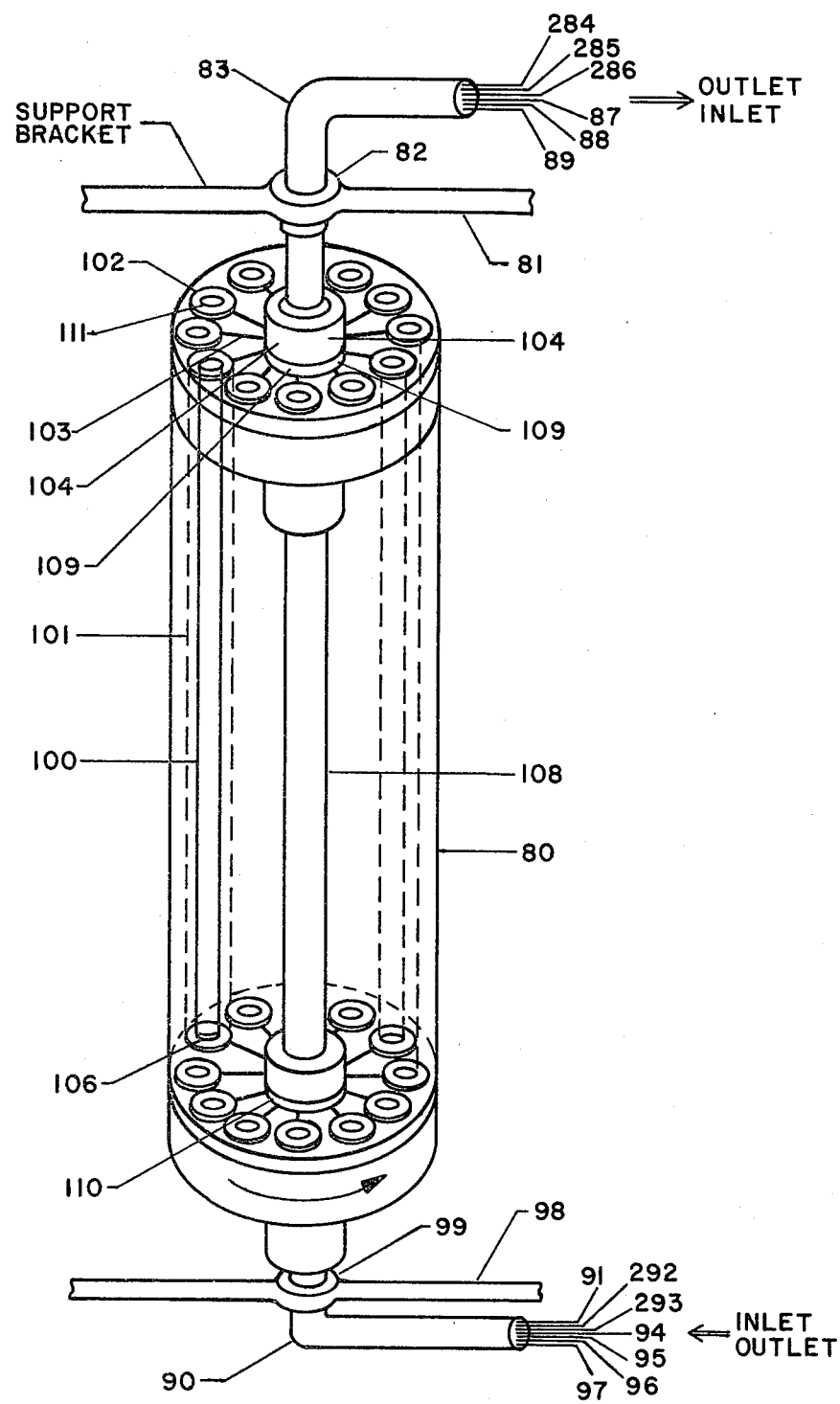
FIG. 4 is a side isometric view of the carousel assembly showing the relationship of the electrophorectic tubes, the fluid connections and the support means.

FIG. 4 provides a side isometric view of the carousel embodiment. The carousel body 80 is supported by brackets 81 and 98 by use of collars 82 and 99. The carousel contains twelve double tube columns arranged in circular fashion around center shaft 108 although smaller or larger numbers of such columns may be employed in alternate embodiments of the invention. A representative double tube column is shown with the electrophoresis tube 100 being supported within external cooling tube 101. Fluid flow connections between the tube electrophoresis and cooling and the central collector assemblies is provided by the ring section assembly 102 and ring section assembly 106 which in turn are connected to the upper collector 109 and the lower collector 110 by conduits 103 and 107 respectively. These conduits provide separate fluid lines for the three fluid inlets and outlets which are utilized at each station and depending on the station may include coolant in or coolant out, buffer in, buffer out, column cleaning or column drying.

Upper collector 109, which rotates with the carousel assembly, is slidably attached to upper port 104 which is stationary. Fluid flow from the six external outlet/inlet connections 84, 85, 86, 87, 88 and 89 is carried by upper fluid port 83 to the upper port 104. The fluid flow interface between the stationary upper port 104 and rotating upper collector 109 employs the disk system described in FIG. 3.

Similarly, the lower collector 110 which also rotates with the carousel assembly is slidably attached to lower port 105 which is stationary. In this instance seven external outlet/inlet connections are connected via lower fluid port 90, i.e., lines 91, 92, 93, 94, 95, 96 and 97. The functions encompassed by these outlet/inlet connections include those enumerated for the upper port plus an added line used to evacuate the contents of the electrophoresis tube.

Introduction of the gradient and the sample into the electrophoresis tube is accomplished by direct access into the tube through top hole 111 which is open to the atmosphere at stations 1 and 2 in the cycle.

Figure 5:
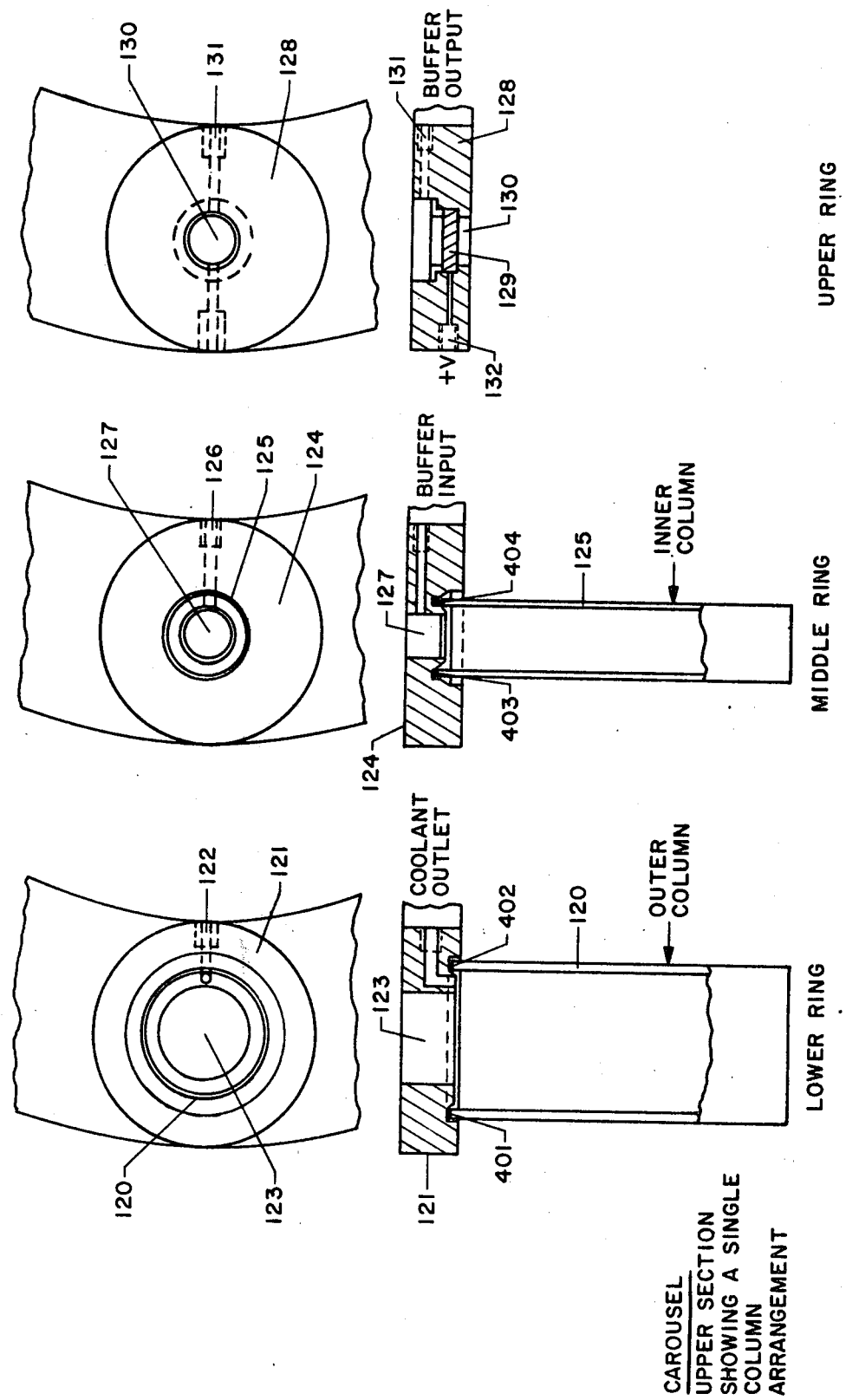
FIG. 5 is a top and cross-sectional view of ring section assembly of the upper section of the carousel showing a single column construction comprising the outer cooling column, the inner gradient electrophoresis column and the electrode assembly and the fluid inlets.

FIG. 5 is a top and cross-sectional view of the ring section assembly of the upper section of the carousel showing the construction of the three ring elements. Thus the top of each outer column such as representative outer column 120 is capped by lower ring 121. The lower ring 121 has a channel 122 which provides a fluid connection from the outer column to the conduit described in FIG. 4. This channel provides an outlet for the coolant which is flowing in countercurrent fashion (from bottom to top) through outer column 120. A central open cavity 123 is provided in the lower ring to allow the inner column to be supported. Thus the lower ring is seen to have a doughnut like construction.

The outer column (and similarly the inner column) are maintained in concentric position by providing cylindrical grooves supplied with flexible gaskets 401, 402, 403 and 404 made of rubber or similar materials and by applying mechanical pressure on both sides of the columns thus making possible the assembly and disassembly of the double columns. Use of mechanical pressure also eliminates the problem of fluid leaking from the contents of the columns.

Middle ring 124 sits upon the lower ring and supports inner column 125. The inner column sits within the outer column so as to be externally cooled by the coolant flowing through the outer column during the entire electrophoresis cycle. The middle ring contains a buffer input channel 126 which is in fluid flow connection with internal chamber 127. During the electrophoresis portion of the cycle, buffer will flow continuously into this chamber. The buffer will be in fluid contact with the top of the gradient in the inner column but due to the difference in densities no substantial mixing will occur. Suitable buffer solutions will comprise mineral acids having high conductivity most preferably dilute sulfuric acid.

The upper ring 128 rests on the middle ring and provides the top electrode assembly. Electrode 129 provided preferably in the form of a hollow cylindrically shaped element and constructed out of any conventional metallic electrode material such as platinum, or paladium, and is supported within center chamber 130 which is in fluid contact with similarly disposed chamber 127. The buffer flow from these chambers outlets through buffer output channel 131. Voltage potential for the electrode is provided through conductive lead 132 which conveniently can be in the form of a metallic wire or screw. Contact with the power supply assembly is achieved through use of a spring or similar contact (not shown on the outer surface of each carousel ring) which engages conductive lead 132 throughout the rotation through the nine stations where electrophoresis takes place, a total of 240° of rotation in the cycle. The voltage employed will generally be about 1000 volts±5% and the maximum current required is approximately 20 mA per column or 180 mA for the nine tubes concurrently undergoing electrophoresis. However, as the carousel rotates the current going through the gradient in the tube is decreased. Thus, prior to reaching the evacuation station, the current through the last column may be in the order of 0.1 to 1.0 mA. Total capability of the power supply is preferably about 250 mA at 1000 volts or 250 watts.

In a further embodiment the power supply can be provided from an A.C. source of variable frequency thus allowing the carousel to be employed for dielectrophoresis. In such embodiment the columns preferably will be provided with an insert of such shape to produce a non-uniform electric field along the length of the column.

It is also possible to utilize an electromagnet as element 129 to provide a magnetic field for the separation of biological sample materials by magnetophoresis where such sample materials are labeled by magnetic microparticle in a manner known in the art.

Figure 6:
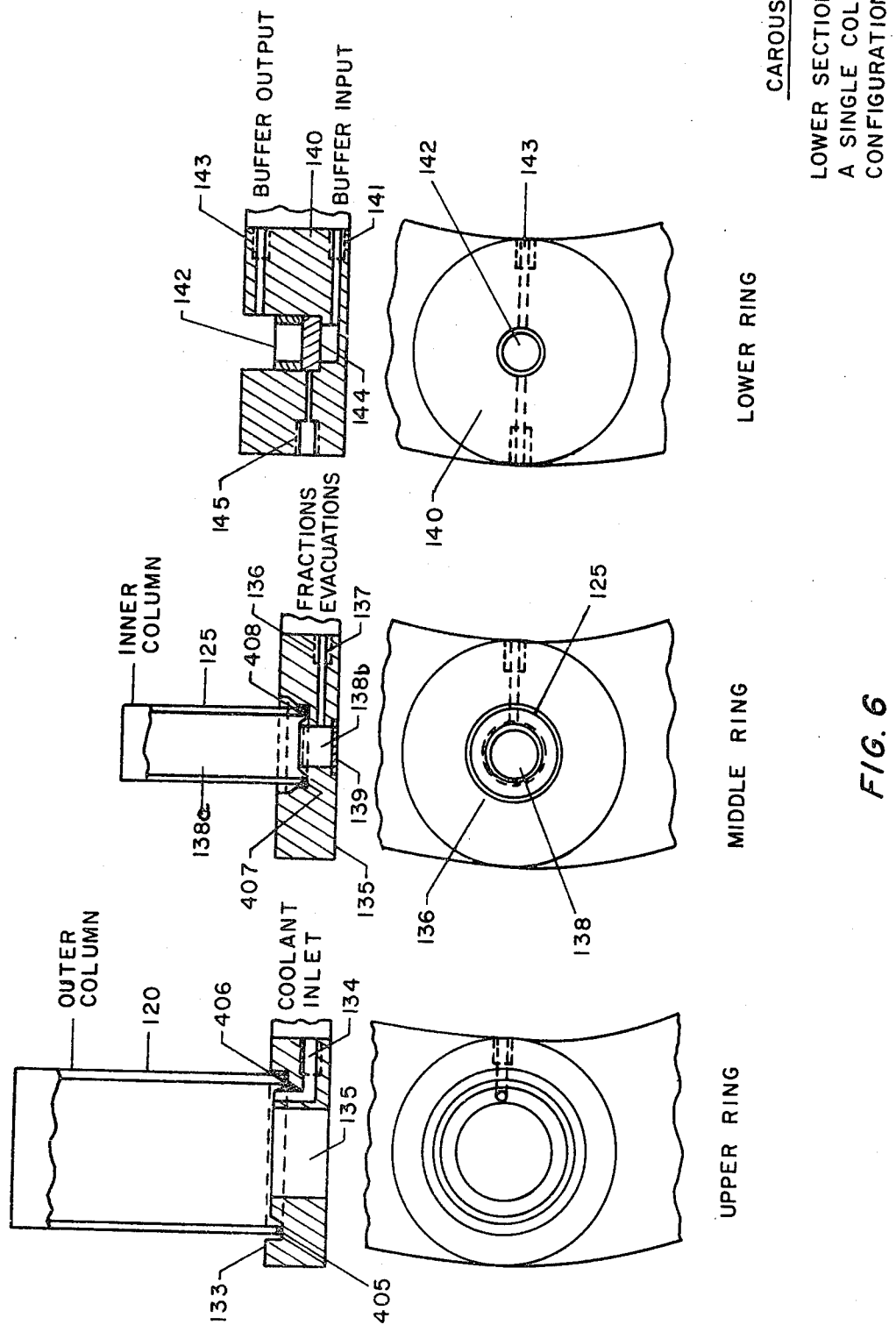
FIG. 6 is a top and cross-sectional view of the ring section assembly of the lower section of the carousel showing a single column construction comprising the outer cooling column, the inner gradient electrophoresis column and the electrode assembly and the fluid inlets for each.

In FIG. 6 a top and cross-sectional view of the ring section assembly of the lower section of the carousel is shown. The upper ring 133 in the lower section supports the base of the outer column 120. Coolant flow is provided into the outer column through coolant inlet channel 134. A central open cavity 135 is provided in the upper ring to allow insertion of the inner column into the outer column.

The middle ring 136 sits beneath and supports the upper ring and also serves as the base for inner column 125. Outlet channel 137 provides fluid flow connection between the internal chamber 138a of inner column 125, via chamber 138b to the external conduit and is used to evacuate the fractions at the evacuation station. A diaphragm 139 is located at the bottom of chamber 138b to provide fluid flow isolation between the sample containing gradient solution and the lower buffer as well as support for the gradient solution. This diaphragm is constructed out of materials which are permeable to ion flow but non-permeable to fluid flow. Suitable semipermeable materials include cellulose acetate, cellophane and porous glass. In this manner ionic conductivity between the two electrodes in each column assembly is maintained.

The lower ring 140 provides support for the lower electrode or in the alternative embodiment the electromagnet 144. Voltage potential for the electrode is provided through conductive lead 145 which is in contact with the external power supply assembly in a directly analogous manner as described for the upper electrode described above. Both the buffer input channel 141 and the buffer output channel 143 are provided in the lower ring. Buffer flow is thus provided through chamber 142 and contacts electrode 144 supported therein. The construction of lower electrode 144 will be the same as described for upper electrode 129 above.

Flexible gaskets 405, 406, 407 and 408 are provided as above to facilitate assembly and disassembly and to provide a leakproof seal.

Figure 7:
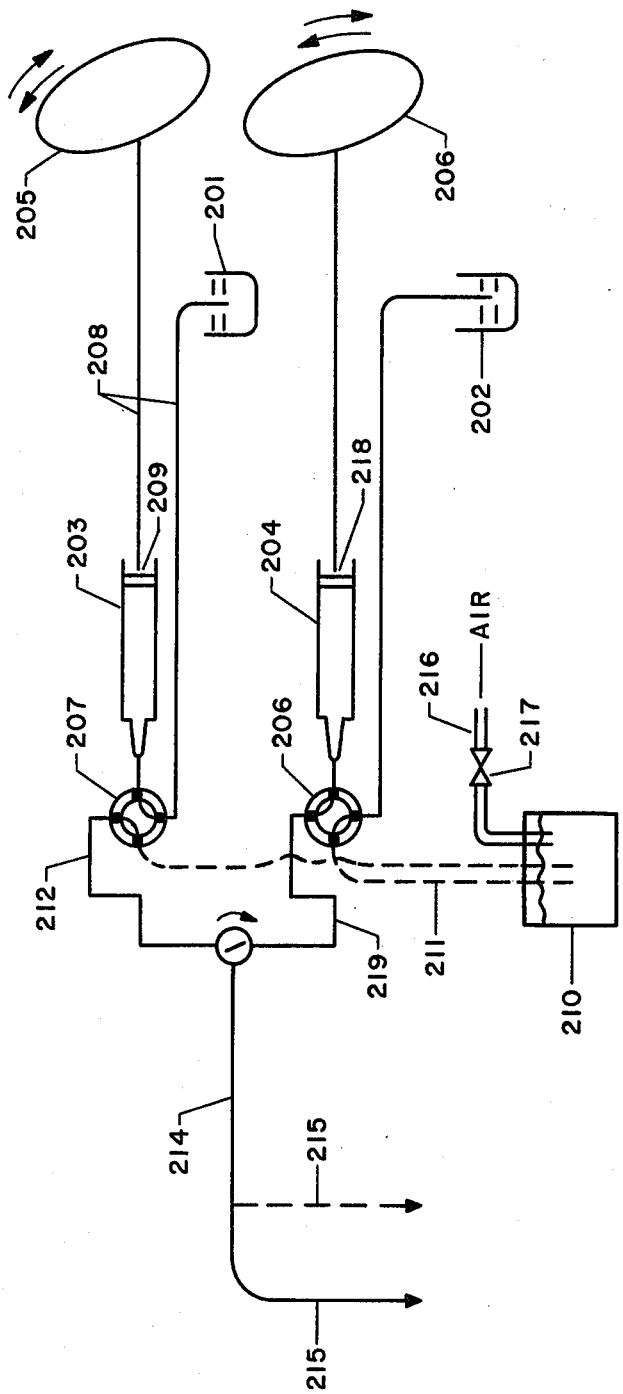
FIG. 7 is a schematic view of one embodiment of a density gradient generator for the first dimensional electrophoresis.

FIG. 7 provides a schematic representation of a density gradient assembly useful in the practice of the present invention. In operation, light and dense solutions (sucrose, Ficoll and the like) are placed in reservoirs 201 and 202, respectively. These solutions are withdrawn into the syringes 203 and 204 by the action of rotating cams or leadscrews 205 and 206 turning by reversible programmable stepping motors (not shown).

In the syringe filling phase two position valve 207 allows the flow of fluid from light solution reservoir 201 through line 208 and into syringe 203 when plunger 209 is withdrawn. At the same time water from reservoir 210 flows through line 211 and through the second port of valve 207, line 212, mixing device 213, line 214 and out to waste through density applicator 215 in the withdrawn position. This procedure serves to clean out the density gradient remaining in the lines from a prior column fill. Water from reservoir 210 is forced up into the system by application of air under mild pressure through line 216 under control of valve 217.

Valve 208 is shown in gradient making positions. In this position plunger 218 is pushed forward into the syringe and the contained dense solution is expelled out through valve 208, line 219 and into mixing device 213. During the filling and mixing procedures both syringes operate in tandem and in the same operating phase. Thus while dense solution is flowing from syringe 204, light solution is flowing from syringe 203. Mixing device 213 mixes the two solutions and the generated gradient is deposited into the electrophoresis column via line 214 and out through applicator 215 in the activated position. The two syringes dispensing fluid at a preprogrammable rate (i.e., unequal linear velocities), so that a linear gradient is generated.

It should be noted that at the start of density gradient generation, a small aliquot of the gradient is allowed to drain to waste by keeping the applicator in the unactivated position at the start of the gradient deposition cycle. This procedure serves to chase out any water present from the rinsing operation in the lines and mixing device. This entire process is repeated each time a new column rotates to the gradient deposition station.

Figure 8:
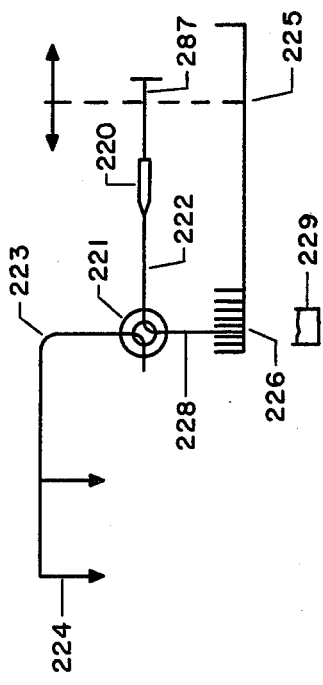
FIG. 8 is a schematic view of one embodiment of a sample applicator assembly for the first dimensional electrophoresis.

FIG. 8 is a schematic representation of the sample applicator assembly. In operation, plunger 227 of syringe 220 is withdrawn thereby withdrawing sample from the sample cuvette 226 in sample holder 225 through needle 228 and valve 221 to the syringe. The sample applicator tip 224 is lowered into the density gradient containing column which has rotated to the sample deposition station.

The sample syringe plunger 227 is pushed forward expelling the sample from syringe 220 through the second port of valve 221, line 223 and then deposited above the gradient in the column through sample application tip 224. Between filling operations the application tip is lifted from the column and moves to the waste position while needle 224 is inserted into water reservoir 229 so as to wash out the system before the system handles the next sample. Such washing procedure in each cycle serves to preserve the integrity of the individual samples.

Figure 9:
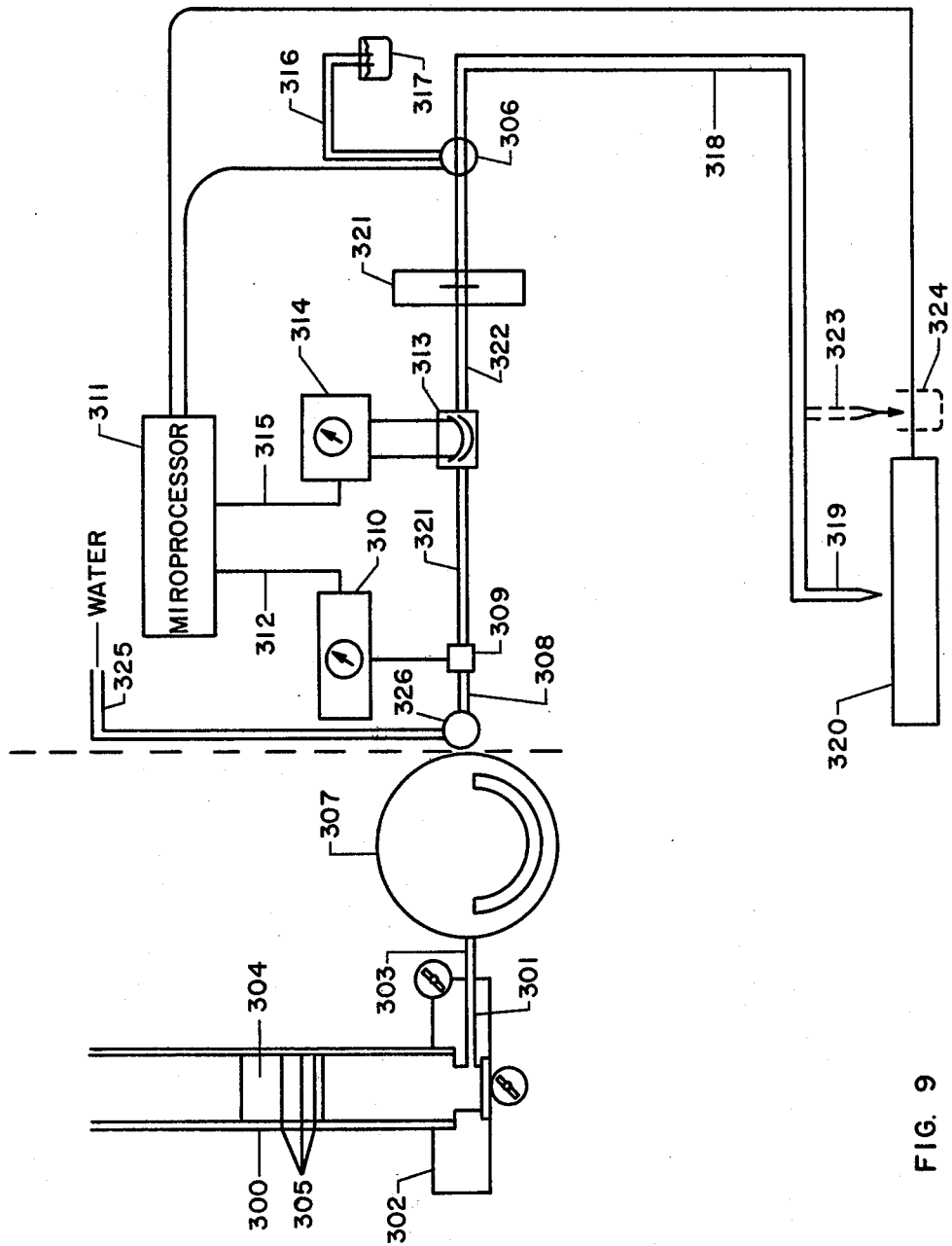
FIG. 9 is a schematic view of one embodiment of the fraction collection assembly of the first dimensional electrophoresis.

The gradient monitoring (column evacuation) assembly is shown in schematic representation in FIG. 9. When a representative electrophoretic column 300 reaches the column evacuation station, the electrophoresis is completed and the electric field is disconnected.

The buffer or electrolyte (in the isoelectric focusing mode) is then evacuated from the buffer chamber contained in the lower ring (see FIG. 6). It is desirable, particularly in the case of isoelectric focusing where the lower chamber is filled with an acid or base, to rinse the chamber with water after evacuation to ensure that the semi-permeable membrane is free of acid or base contamination. At this time automatic valve 306 opens and directs the flow of gradient out of column 304, through channel 301 in middle ring 302 of the lower section (see FIG. 6), out through line 303 and lower collector assembly 307 (shown in representational manner—see FIG. 3c for detail) where it passes through the fraction evacuation channel and leaves the rotating section and out the stationary assembly via line 308. The gradient then is passed through flow cell 309 of UV or fluorescence monitor 310 where the contents are monitored and anayzed and the output provided by electronic signal to microprocessor 311 by electronic connector 312. A second flow cell 313 lies downstream of the UV or fluorescence monitor. This second flow cell containing pH recording electrodes detects the pH of the passing gradient and it is measured by pH meter 314. The resulting signals are also fed to microprocessor 311 by electronic connector 315.

It is also possible to employ as alternate monitoring means one or more of the following: a light scattering monitor, refractive index monitor, or an electrical resistance monitor. Instrumentation for providing such monitoring are well known in the art.

Depending on the nature of the information received by the microprocessor, valve 306 is controlled to either pass the flowing gradient out through line 316 and then out to waste or upon sensing the presence of a desired component in the gradient or a preselected pH value in the gradient, the valve 306 is controlled to pass the gradient through line 318 and out through outlet tip 319 into a cuvette held by fraction collector 320.

The flow rate of column evacuation can be controlled by use of a flow controller 321 which can be either (a) a peristaltic pump, the rotational velocity of which is controlled by the microprocessor, or (b) by an adjustable flow rate restrictor of the rotational type. In the case (b) the microprocessor will control the speed of the restrictor, thus reducing the opening allowed for flow, so that a constant flow rate is obtained. This is necessary because the density gradient becomes gradually less viscous (towards the top of the column) and thus, its flow rate characteristics are accordingly increased. The microprocessor and control module will allow for the selection of various flow rates, for flexibility of application when gradients of different chemical nature are used (e.g., surose, Ficoll etc.).

The volume of liquid in line 321 between flow cells 309 and 313 is known by using loop-tubing of certain dimensions. This parameter is inputted into the microprocessor.

The microprocessor in receiving an analog signal from the pH meter and after A/D conversion will process the digital information in terms of the following:
(a) starting pH: the pH at which collection of fractions is to be initiated.
(b) terminating pH: the pH at which collection of fractions is to be terminated.
(c) pH segment: the desired pH value difference between two consecutive fractions.
(d) number of fractions to be collected (up to the maximum allowed by the fraction collector, i.e., $12 \times 50 = 600$).

The following mode of collection will be available:

Mode I

Preset:
staring pH (s)
terminating pH (t)
number of fractions to be collected (n).
Collection mode:
pH segment = (t-s)/n.
Example:
Start collecting at pH 4.0, terminate at pH 6.0, and collect 20 fractions.
Result: the fractions will differ by 0.1 pH unit.

Mode II

Preset:
starting pH (s)
pH segment (d)
number of fractions to be collected (n)
terminating pH = s + d n
Example:
Start collecting at pH 5.0, collect fractions differing by 0.05 pH units, collect 50 fractions.
Result: terminating pH = 7.5.

Mode III

Preset pH segment (d)
Result: Fractions are collected differing by d pH units starting with the first fraction.

Mode IV

Preset: volume of fraction
Result: Fractions of certain volume are collected regardless of pH consideration. Useful in electrophoresis and other fractionations where a pH gradient is not involved.

Other modes of operation in addition to the above are possible. For example, if one runs only six columns on the carousel, the collection can be switched to the second cassette (thus, up to 100 fractions can be collected per column, with a maximum possible of 600 for one column on the carousel).

After pH recording of the gradient flow and following the programmed microprocessor logic for each mode of operation, the following occur: (a) At the starting pH (s) the valve 306 is activated to direct the flow to the fraction collector 320 and the sample is collected. When flow cell 313 is recording (s+d) pH units the fraction collector is activated to change position to collect the next fraction. (When starting pH has not been specified, the pH of the very first volume of the gradient will be considered as starting pH), (b) the average pH and average absorbance of the first fraction is computed by the microprocessor and stored in memory, (c) these values are printed-out in tabular form with a printer and after D/A conversion are used to plot absorbance (or transmittance) and pH curves in a 2-channel recorder along with the event mark of fraction change.

The pH cell and UV cell are recording the properties of the gradient differing by certain volume, the loop 322. However, since the flow rate is constant and the volume of 302 is known, the correct (average) absorbance of a sample of certain (average) pH value can be assigned to the sample by taking this value from the microprocessor memory.

In the case samples are collected by volume, activation of the valve 306 and the fraction collector 320 will be based on microprocessor control only; because the flow rate (ml/sec) is known and the volume of each fraction (ml) is preset, the time of collection of each fraction can be estimated by the machine.

After collection of the last fraction, there is a need to rinse the tubing from collector 307 to tip 319 and to fill with water so that the flow cells will not dry out (especially the pH cell). This is performed automatically by positioning the tip of the collecting tubing 319 to the offset position 323 where there is a waste container 324. Water from inlet 325 is directed by way of the valve 326 into tubing 308 and exists into waste 324. Valve 326 after the rinsing operation is switched to the other position to allow flow of gradient from the next column.

The tip 319 is placed in the appropriate position in the fraction collector 320 to be ready for collecting the second column position. Valve 306 is placed in the closed position. The above cycle is repeated for the next column.

FIG. 10 provides a front view of the sample holder fraction collector: The tip 319 is placed in position No. 1 of the sample holder 327 and deposited in cuvette or well 328 which ends in a capillary opening 329. The sample does not leak out of the wells because of the small orifice. The fractionated samples are collected sequentially in the wells. A cover plate 330 is placed on top of holder 327 and mild pressure is applied through tubing 331 to evacuate the sample from the wells into the gel slots of the second dimension electrophoresis system.

FIG. 11 shows a front view of a volume equalizing device use in conjunction with the sample holder. Excess sample (above predetermined volume) is removed by wire needles such as 332 into reservoir 333 which is connected by means of needle 334 to mild vacuum manifold 335.

As seen in end view of the volume equalizing device in conjunction with the sample holder in FIG. 12 each well has a corresponding collecting reservoir such as 337. After sample collection, the sample collector 327 is placed on top of the second dimension polyacrylamide gel slab bearing sample slots corresponding to the position of the tips, i.e., 329.

The sample collector is then removed and electrophoresis is initiated after overlaying with buffer. Since the collected samples have higher density than the buffer, they stay at the bottom of the slots.

The excess sample collected in reservoirs of volume equalizer 333 is forced by mild pressure applied by means of manifold 337 and needle 334 to be evacuated into storage vials.

Figure 13:
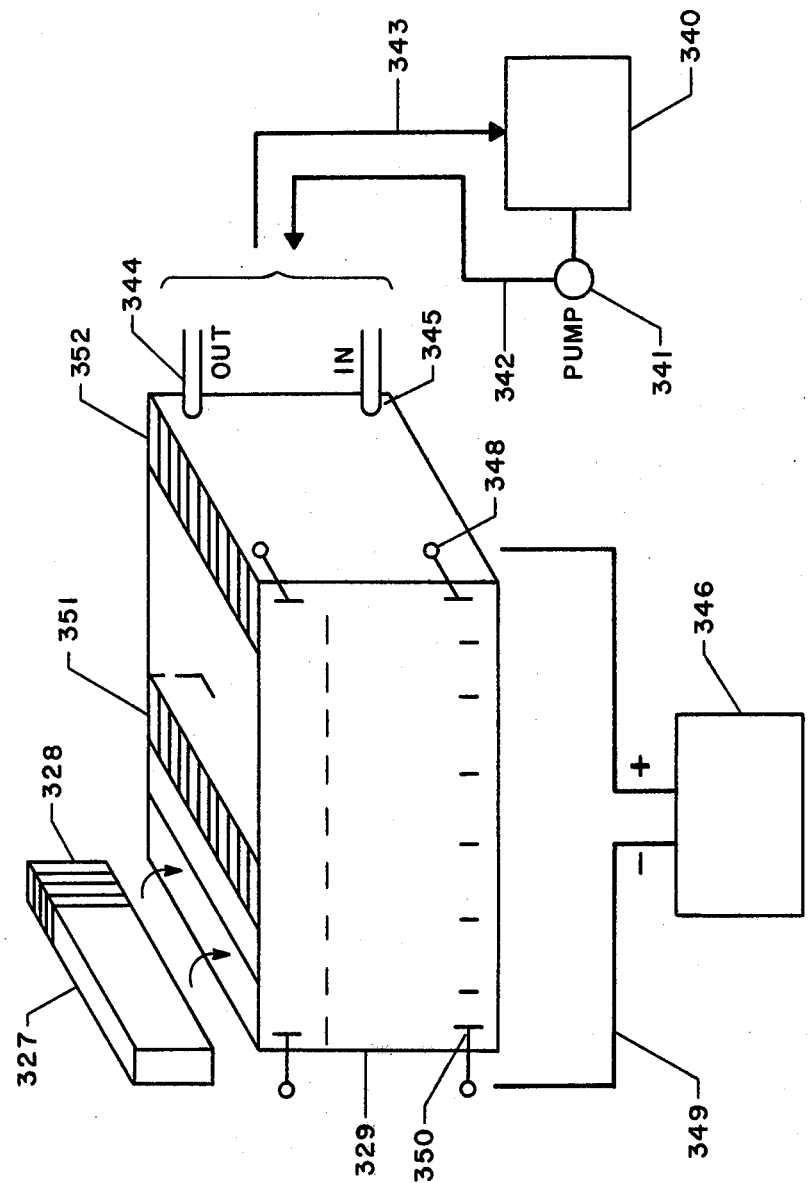
FIG. 13 is a diagrammatic view of the second dimensional system showing the multiple fraction collector cassettes filling atop the second dimensional gels supported within the electrophoresis tank.

FIG. 13 is a diagrammatic view of the second dimensional system. The second dimension electrophoresis may be run on any medium conventionally employed in gel electrophoresis. A particularly preferred medium is a polyacrylamide gel which is in the form of a slab. The gel may optionally contain a small amount of a detergent such as sodium dodecyl sulfate. Such gels consist of two gel phases (a stacking gel and a separating gel) or a density gradient polyacrylamide gel both of which are articles of commerce.

To provide sample application for the second dimension the sample holder 327 containing the fractions separated during the first dimensional electrophoresis run and maintained in individual cuvettes or compartments such as 328 is attached to a gel slab such as 351 or 352 supported vertically in the tank 339. The tank will preferably support the same number of gel slabs as there are columns in the carousel preferably 12. Sample is transferred by covering the holder with and applying positive pressure to the manifold cover described in FIG. 10. Once sample transfer to the gel is completed, the second dimension electrophoresis is initiated.

The second dimensional electrophoretic process has the same power requirement as was employed in the first dimension. Thus the applied voltage will be of the same value while the total current requirements will be in about 60 mA. It is thus possible, if desired, to use the same power supply, i.e., 346 for both dimensions. Potential is applied to different sides of tank 339 by means of line 347 and electrode 348 and line 349 and electrode 350. Coolant is provided from reservoir 340 by means of pump 341, line 342 and inlet 345. The coolant surrounds the suspended slabs by countercurrent flow and exits by means of outlet 344 and line 343 where it is returned to the reservoir.

Upon completion of the electrophoresis the potential is removed from the tank and the slabs are removed. Visualization can be accomplished using procedures well known in the art. Thus the slabs may be treated with a stain selective for the materials being separated which stain can be detected colorimetrically or by fluorescence. Alternatively it is possible to utilize radiolabelled samples using radioactive isotopes and detecting the separated components by autoradiography. If the second dimensional analysis is run in a preparative mode sections of gel containing desired samples can be cut out and the sample extracted and recovered by use of appropriate solvents.

The two dimensional electrophoresis system of the present invention is primarily constructed using parts fabricated from nonreactive durable plastic, glass, synthetic rubber and stainless steel materials which are chemically resistant to all reagents currently in use in electrophoresis.

While the two dimensional system of the present invention has been described as operating as a single integrated unit it is possible to utilize individual assemblies and sub-systems as stand alone devices. In one such embodiment the carousel can be utilized in the absence of electrodes and the resulting potential field to separate biological cells by gravity sedimentation.

I claim:

1. An integrated electrophoresis system which comprises in combination
A. a first dimensional electrophoresis sub-system comprising in combination
   (i) carousel means containing a multiplicity of electrophoresis columns rotatable circularly through a multiplicity of stations wherein one or more of said stations is associated with functions consisting of electrophoresis medium deposition, sample deposition, electrophoresis, electrophoresis medium evacuation, and column washing and drying;
   (ii) electrophoresis medium deposition means, said means being in operative fluid flow relationship with each of said electrophoresis column which is positioned in said electrophoresis medium deposition station whereby electrophoresis medium is provided to each such column;
   (iii) sample deposition means, said means being in operative fluid flow relationship with each of said electrophoresis columns which is positioned in said sample deposition station whereby individual samples are provided to the top of the electrophoresis medium in each said column;
   (iv) electrophoresis means comprising power supply means, electrode means and electrical connector means whereby said electrode means are in ionic contact with said electrophoresis medium in each column and said electrical connector means provides continuous electrical connection between said power supply means, and said electrode means while said column is passing between said electrophoresis stations so as to provide a voltage potential across said electrophoresis medium suitable for carrying out electrophoretic separations;
   (v) electrophoresis medium monitoring means, said means being in operative fluid flow relationship with said electrophoresis medium evacuation station whereby the electrophoresis medium after completion of the electrophoresis is removed from said carousel and is monitored for location of desired sample by measurement of one or more selected parameters;
   (vi) column washing and drying means, said means being in fluid flow relationship with said column washing and drying station whereby each column in such station after evacuation of electrophoresis medium is cleaned and prepared for electrophoresis medium deposition at the initial station of the next cycle;
   (vii) fraction collection means, said means being in operative fluid flow relationship with said electrophoresis medium monitoring means whereby said monitored electrophoresis medium is divided into multiple selected discrete fractions and said fraction collection means containing a sample holder means so arranged and constructed as to serve as a sample holder and applicator means for the second dimensional electrophoresis; and
   (viii) cooling fluid means, said means being in operative fluid flow relationship with cooling columns which surround each of said electrophoresis columns in said carousel whereby cooling fluid is provided to said cooling columns throughout the entire rotational cycle of said carousel to thereby remove the heat generated by said electrophoresis;
B. a second dimensional electrophoresis sub-system comprising in combination;
   (i) slab gel holder tank means so arranged and constructed as to be capable of supporting a multiplicity of slab gels suitable for gel electrophoresis, said slab gels being maintained in a position allowing for sample administration employing said sample holder means from the said first dimensional fraction collector means whereby the discrete fractions collected from said first dimensional electrophoresis are applied to said slab gels;

(ii) power supply means, said means being in electrical contact with said slab gel holder tank means whereby a potential suitable for carrying out gel electrophoresis is established across said gels; and (iii) cooling fluid means, said means being in operative fluid flow relationship with said slab gel holder tank means whereby heat generated by said gel electrophoresis is removed;

C. microprocessor control means, said means being in operative electrical contact with the components of each said sub-system so as to provide operative process control over such sub-systems.

2. The system of claim 1 wherein said carousel is operatively connected to a stepping motor which upon activation serves to rotate said columns from station to station.

3. The system of claim 2 wherein twelve electrophoresis columns are provided on said carousel and said stepping motor steps 30° upon each activation.

4. The system of claim 1 wherein said electrophoresis medium deposition means comprise a gradient density maker whereby varying proportions of solutions of two selected densities are mixed to generate electrophoresis medium having a density which varies linearly between the densities of said two solutions.

5. The system of claim 4 wherein said solutions consist of a density generating media selected from sucrose and Ficoll in varying concentrations.

6. The system of claim 1 wherein said sample deposition means comprises a sample collector employing X-Y positioning to withdraw individual samples from separate sample holder cuvettes.

7. The system of claim 1 wherein said fraction collection means divides said evacuated electrophoresis medium into discrete fractions based on passage of a preselected volume of such medium.

8. The system of claim 1 wherein said electrophoresis medium monitoring means is selected from one or more of the following monitors, U.V. monitor, fluorescence monitor, light scattering monitor, refractive index monitor, electrical resistance monitor and pH monitor wherein a preselected parameter level read by said monitors is utilized to divide said evacuated electrophoresis medium into discrete fractions which are provided to said sample holder means.

9. The system of claim 8 wherein volume equalizing means are provided whereby the sample volumes for each of said fractions contained in said sample holder means are adjusted to a single, preselected value prior to said sample holder's being employed as a sample applicator for the second dimensional electrophoresis.

10. The system of claim 1 wherein said sample holder means is so arranged and constructed as to provide for storing up to fifty discrete fractions.

11. The system of claim 10 where each such discrete fraction is maintained in a separate chamber, said chamber having a capillary tube as a base whereby said fraction is held in said chamber by capillary tension and is passed out through such capillary tube upon application of pressure to such chamber.

12. The system of claim 1 wherein said first dimensional sub-system is so constructed and arranged as to be suitable for carrying out dielectrophoresis.

13. The system of claim 1 wherein said first dimensional sub-system is so constructed and arranged as to be suitable for carrying out magnetophoresis.

14. A carousel comprising in combination:

A. a centrally disposed rotatable shaft having an upper end and a lower end, said upper end being attached to an upper collector assembly comprising a lower cylindrical body and an attached upper cylindrical body of smaller circumference than said lower body, said upper body containing a multiplicity of vertical channels passing through said body, said vertical channels being arranged in three concentric rings, each ring containing an equal number of channels and said lower body containing an equivalent number of horizontal channels said horizontal channels being so arranged and constructed as to intersect perpendicularly with a corresponding vertical channel so as to form a multiplicity of fluid pathways from the top of said upper body to the sides of said lower body, and said lower end of said shaft being attached to a lower collector assembly of identical construction as said upper collector assembly but mounted in an inverse manner on said shaft;

B. a number of double concentric columns attached circumferentially about and outwardly from said shaft, said number of double columns being equal to the number of channels in any one ring in said collector assemblies, each of said double columns consisting of an inner electrophoresis column and an outer coolant column, the upper section of said double columns being in operative attachment with an upper section ring assembly consisting of a lower ring engaging the upper part of said outer column and having a centrally disposed cylindrical cavity of a circumference greater than said inner column and a channel extending from one side of said ring to the bottom of said ring so as to be in fluid flow relationship to the internal portion of said outer column, a middle ring engaging the upper part of said inner column and having a centrally disposed cylindrical chamber, the bottom of said chamber being in open fluid flow contact with the top of the inside of said inner column and a channel extending from one side of said ring to said cylindrical chamber, and an upper ring engaging the top of such middle ring and having a centrally disposed chamber and a channel extending from one side of said ring to said chamber and the lower section of said double columns being in operative attachment with a lower ring assembly consisting of an upper ring engaging the lower part of said outer column and having a centrally disposed cylindrical of a circumference greater than said inner column and a channel extending one side of said ring to the top of said ring so as to be in fluid flow relationship to the internal portion of said outer column, a middle ring engaging the lower part of said inner column and having a centrally disposed cylindrical chamber, the top of said chamber being in open fluid flow contact with the inside bottom of said inner column and the bottom of said chamber being sealed by a cylindrical semipermeable membrane means which prevents fluid flow but allows passage of ions and a channel extending from one side of said ring to said chamber and a lower ring engaging the bottom of said middle ring and having a centrally disposed chamber, a first channel extending from one side of said ring to the upper portion of such chamber and a second channel extending from said side of said ring to the lower portion of such chamber;

C. fluid conduit means extending spoke like from each of the channels opening on the sides around each of said upper and lower collector assemblies to the channels in each of the said upper section rings and lower section rings to provide fluid flow connection between such channels;

D. fluid flow control means engaging each of said upper and lower collector assemblies comprising a non-rotatable port means having a number of vertical channels so arranged and constructed so that at least one of said vertical channels is in a position opposing the channel rings contained in said collector assemblies, stationary disk means associated with said non-rotatable port means said disk having grooves or holes arranged around concentric rings said grooves or holes being of pre-selected patterns and being so arranged and constructed to oppose the channel rings on said port means, rotating disk means associated with said collector assembly and being slidably engaged with said stationary disk means said rotating disk means having a multiplicity of holes arranged in concentric rings, the number of holes in each such ring being equal to the number of inner columns and the number of channels in each ring of said collector assembly, whereby as said collector assembly and associated disk rotate, their holes and directly opposed channels are either in operative fluid flow relation with holes or groves in said stationary disk means and the opposing channels in said port means or said fluid flow is blocked thus providing pre-selected fluid flow patterns in said channels.

15. The carousel of claim 14 wherein each of the rings of both said stationary and rotating disks are maintained in fluid flow isolation from the other rings in said disks by an interposing-circular plastic washer placed between each such rings.

16. The carousel of claim 14 wherein a first electrode means or electromagnet means extends transversly across the said centrally disposed chamber below said channel in said upper ring of said upper section ring assembly and wherein a second electrode means or electromagnet means extends transversly across the said centrally disposed chamber between said channels in said lower ring of said lower ring assembly each of said electrode means or electromagnet means being in contact with respective first and second conductive means which extend through said respective rings to their respective sides.

17. The carousel of claim 16 wherein each of said first and second conductive means engage power supply means at preselected zones during rotation of said carousel.

18. The carousel of claim 14 wherein said double columns are maintained in concentric position by mechanical pressure exerted between said upper section ring assembly and said lower section ring assembly.

* * * * *